United States Patent
Binier

(10) Patent No.: US 10,376,205 B1
(45) Date of Patent: Aug. 13, 2019

(54) ELECTRONIC TUNING FORK DEVICE

(71) Applicant: INNOVATIVE PRECISION INSTRUMENTS LIMITED, Hong Kong (HK)

(72) Inventor: Richard Jean Marie Binier, Taipei (TW)

(73) Assignee: INNOVATIVE PRECISION INSTRUMENTS LIMITED, Hong Kong (HK)

( * ) Notice: Subject to any disclaimer, the term of this patent is extended or adjusted under 35 U.S.C. 154(b) by 0 days.

(21) Appl. No.: 16/190,489

(22) Filed: Nov. 14, 2018

(51) Int. Cl.
| | |
|---|---|
| *H03B 5/30* | (2006.01) |
| *A61B 5/00* | (2006.01) |
| *H03G 3/30* | (2006.01) |
| *G06F 3/16* | (2006.01) |
| *H04R 1/02* | (2006.01) |

(52) U.S. Cl.
CPC .......... *A61B 5/4827* (2013.01); *A61B 5/0051* (2013.01); *A61B 5/4029* (2013.01); *G06F 3/165* (2013.01); *H03G 3/30* (2013.01); *H04R 1/028* (2013.01)

(58) Field of Classification Search
CPC ... A61B 5/4827; A61B 5/4029; A61B 5/0051; H04R 1/028; H03G 3/30; G06F 3/165
USPC .................................................. 331/37, 156
See application file for complete search history.

(56) References Cited

U.S. PATENT DOCUMENTS

2005/0124910 A1    6/2005  Gupta

FOREIGN PATENT DOCUMENTS

| CN | 200986808 Y | 12/2006 |
| CN | 102438506 A | 3/2010 |
| CN | 102144925 A | 12/2010 |
| CN | 105266758 A | 7/2014 |

(Continued)

*Primary Examiner* — Richard Tan
(74) *Attorney, Agent, or Firm* — Kramer Amado, P.C.

(57) ABSTRACT

An electronic tuning fork device including a control unit including a processor, electrically connected to an input unit and the display component, wherein the processor is configured to generate a first square wave signal and determine a gain parameter according to a predetermined mode, wherein the gain parameter is a value selected from between a predetermined maximum value and a predetermined minimum value, a frequency divider electrically connected to the processor, configured to down-convert the first square wave signal and output a second square wave signal, a first waveform conversion circuit, electrically connected to the processor, configured to convert the first square wave signal into a first sine wave signal, a second waveform conversion circuit, electrically connected to the frequency divider, configured to convert the second square signal into a second sine wave signal, a mixer, electrically connected to the first and second waveform conversion circuits, configured to mix the first sine wave signal and the second sine wave signal and output a sine wave signal, and a gain control circuit, electrically connected to the processor and the mixer, configured to change the amplitude of the sine wave signal according to the gain parameter, wherein when a control signal is generated, the processor receives the control signal and determines a corresponding gain parameter, the processor calculates the measurement result according to the corresponding gain parameter, the predetermined maximum value and the predetermined minimum value.

10 Claims, 4 Drawing Sheets

(56) References Cited

FOREIGN PATENT DOCUMENTS

JP 63-94128 A 4/1988
WO 2016/185191 A1 11/2016

ELECTRONIC TUNING FORK DEVICE

TECHNICAL FIELD

This disclosure relates generally to a perception testing device and more particularly, but not exclusively, to an electronic tuning fork device for testing a vibration perception of a patient.

BACKGROUND OF THE INVENTION

In recent years, the incidence of diabetes has increased year by year in patients and one of the common conditions of diabetes is diabetic foot, which is a serious chronic complication. One of the main causes for diabetic foot are lesions of the sensory nerve, motor nerve and peripheral arterial blood vessels. Diabetic foot causes the foot tissue to become necrotic due to the lack of blood circulation and may even require amputation of the foot in severe cases.

Symptoms of diabetic lesions of motor nerves are mainly on the peripheral nerves. The more severe condition could lead to loss of feeling in a patient's foot, such that that the sense protection function of that foot would be lost, which may be a cause of diabetic foot ulcers.

Diabetes patients are often unable to properly detect abnormal limbs, and many patients even lose their sense protection function in their foot, meaning that they perceive their peripheral circulation to be normal when it is abnormal.

Therefore, medical staff cannot diagnose whether diabetes patients are losing their sense protection function in their foot merely by asking the patient, instead medical staff often use a mechanical tuning fork to test the vibration perception of their foot.

When testing, a patient is asked to close their eyes, while the medical staff knocks the mechanical tuning fork to vibrate and places the tuning fork on the joint or nail of the patient's foot. Then, the medical staff asks the patient whether he/she can sense the vibration. If the patient cannot feel the vibration, the medical staff reads the scale shown on the mechanical tuning fork. If the scale is greater than or equal to 5, then the patient's vibration perception is normal, however, if the scale is less than 5 or no vibration at all, then the patient's vibration perception is abnormal.

However, when using a mechanical tuning fork for testing a patient's vibration perception, the medical staff must read the scale on the mechanical tuning fork with their naked eyes, causing the result of the test to be subjective, the data (e.g., reading the scale) may be prone to error and misjudgments may occur. In addition, traditional mechanical tuning forks may be limited to the medical staff with measurement experience, and therefore cannot be performed by a lay person, such as family members or friends of diabetic patients to help perform the test on the diabetes patients at home.

SUMMARY OF THE INVENTION

A brief summary of various embodiments is presented below. Embodiments address the need to create an electronic tuning fork device.

In order to overcome these and other shortcomings of the prior art and in light of the present need to create an electronic tuning fork device, a brief summary of various exemplary embodiments is presented. Some simplifications and omissions may be made in the following summary, which is intended to highlight and introduce some aspects of the various exemplary embodiments, but not to limit the scope of the invention.

Detailed descriptions of a preferred exemplary embodiment adequate to allow those of ordinary skill in the art to make and use the inventive concepts will follow in later sections.

Various embodiments described herein relate to an electronic tuning fork device, which includes a control unit including a processor, electrically connected to an input unit and the display component, wherein the processor is configured to generate a first square wave signal and determine a gain parameter according to a predetermined mode, wherein the gain parameter is a value selected from between a predetermined maximum value and a predetermined minimum value, a frequency divider electrically connected to the processor, configured to down-convert the first square wave signal and output a second square wave signal, a first waveform conversion circuit, electrically connected to the processor, configured to convert the first square wave signal into a first sine wave signal, a second waveform conversion circuit, electrically connected to the frequency divider, configured to convert the second square wave signal into a second sine wave signal, a mixer, electrically connected to the first and second waveform conversion circuits, configured to mix the first sine wave signal and the second sine wave signal and output a sine wave signal, and a gain control circuit, electrically connected to the processor and the mixer, configured to change the amplitude of the sine wave signal according to the gain parameter, wherein when a control signal is generated, the processor receives the control signal and determines a corresponding gain parameter, the processor calculates the measurement result according to the corresponding gain parameter, the predetermined maximum value and the predetermined minimum value.

In an embodiment of the present disclosure, the electronic tuning fork device, further includes a display component, configured to display a measurement result, the control unit being configured to control a vibration of a vibration component, a power amplifying circuit, electrically connected to the gain control circuit and the vibration component, configured to amplify an output signal of the gain control circuit, and a battery component, electrically connected to the processor, the gain control circuit and the power amplifying circuit.

In an embodiment of the present disclosure, in the predetermined modes, the gain parameter gradually decreases from the predetermined maximum value to the predetermined minimum value within a predetermined time.

In an embodiment of the present disclosure, in the predetermined modes, the gain parameter gradually increases from the predetermined minimum value to the predetermined maximum value within a predetermined time.

In an embodiment of the present disclosure the input unit includes a remote transmitter, configured to transmit a wireless signal and a remote receiver, electronically connected to the processor, and configured to receive the wireless signal.

In an embodiment of the present disclosure, the vibration component is a vibration speaker.

In an embodiment of the present disclosure, the control unit further includes a wireless communication circuit, wherein the wireless communication circuit is electronically connected to the processor, and is configured to wirelessly transmit the measurement result to an external device.

In an embodiment of the present disclosure, the electronic tuning fork device further including a speaker, wherein the speaker is electronically connected to the processor, and is configured to play the measurement result in a voice manner.

In an embodiment of the present disclosure, the square wave signal has a fixed frequency.

In an embodiment of the present disclosure, the measurement result is related to a ratio of the corresponding gain parameter and the predetermined maximum value or related to a ratio of the corresponding gain parameter and the predetermined minimum value.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

These and other more detailed and specific features of the present invention are more fully disclosed in the following specification, reference being had to the accompanying drawings, in which.

Figure 1:
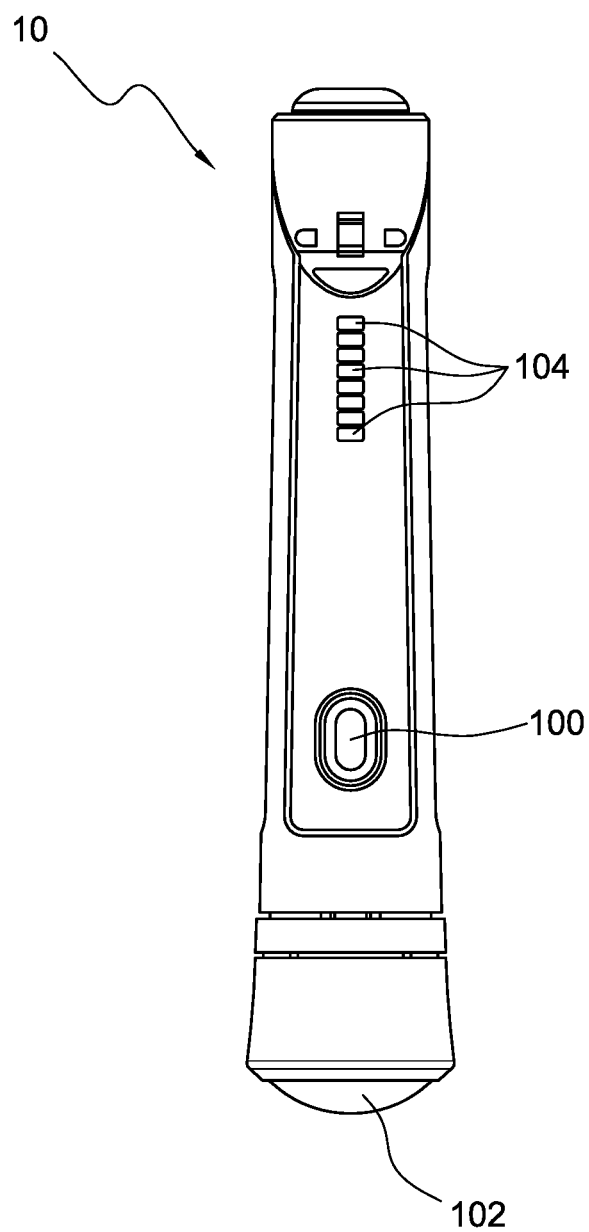
FIG. 1 illustrates a side view of an electronic tuning fork device of the current embodiment.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. Descriptors such as "first," "second," "third," etc., are not meant to limit the order of elements discussed, are used to distinguish one element from the next, and are generally interchangeable.

FIG. 1 illustrates a side view of an electronic tuning fork device of the current embodiment. FIG. 1 illustrates that the electronic tuning device of the present invention has a pen-shaped appearance. The electronic tuning fork device 10 includes a display component 104, an input unit 100 and a vibration component 102.

Figure 2:
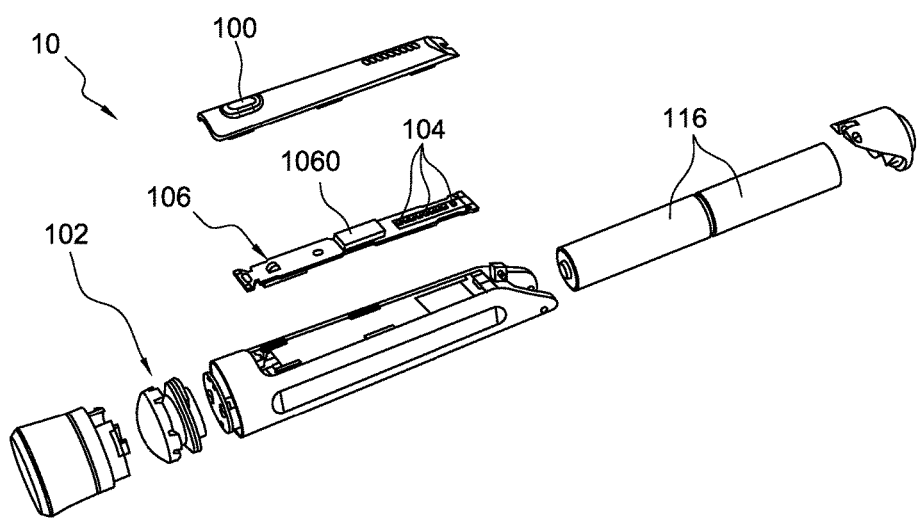
FIG. 2 illustrates an exploded view of the electronic tuning fork device of FIG. 1 of the current embodiment.

FIG. 2 illustrates an exploded view of the electronic tuning device of FIG. 1 of the current embodiment.

The electronic tuning fork device 10 includes an input unit 100, a vibration component 102, a display component 104, a control unit 106 and a battery component 116. The input unit 100 may be a button or a module including a remote transmitter and a remote receiver, in which the remote transmitter is configured to transmit a wireless signal, and the remote receiver being electrically connected to a processor 1060 that is configured to receive a wireless signal.

The vibration component 102 is disposed at the distal end of the electronic tuning fork device 10, and is configured to make contact with a testing portion of a patient. In an embodiment of the present invention, the vibration component 102 may be a vibration speaker.

The display component 104 is configured to display a measurement result, and may be a liquid crystal display or a light emitting diode ("LED") display.

Figure 3:
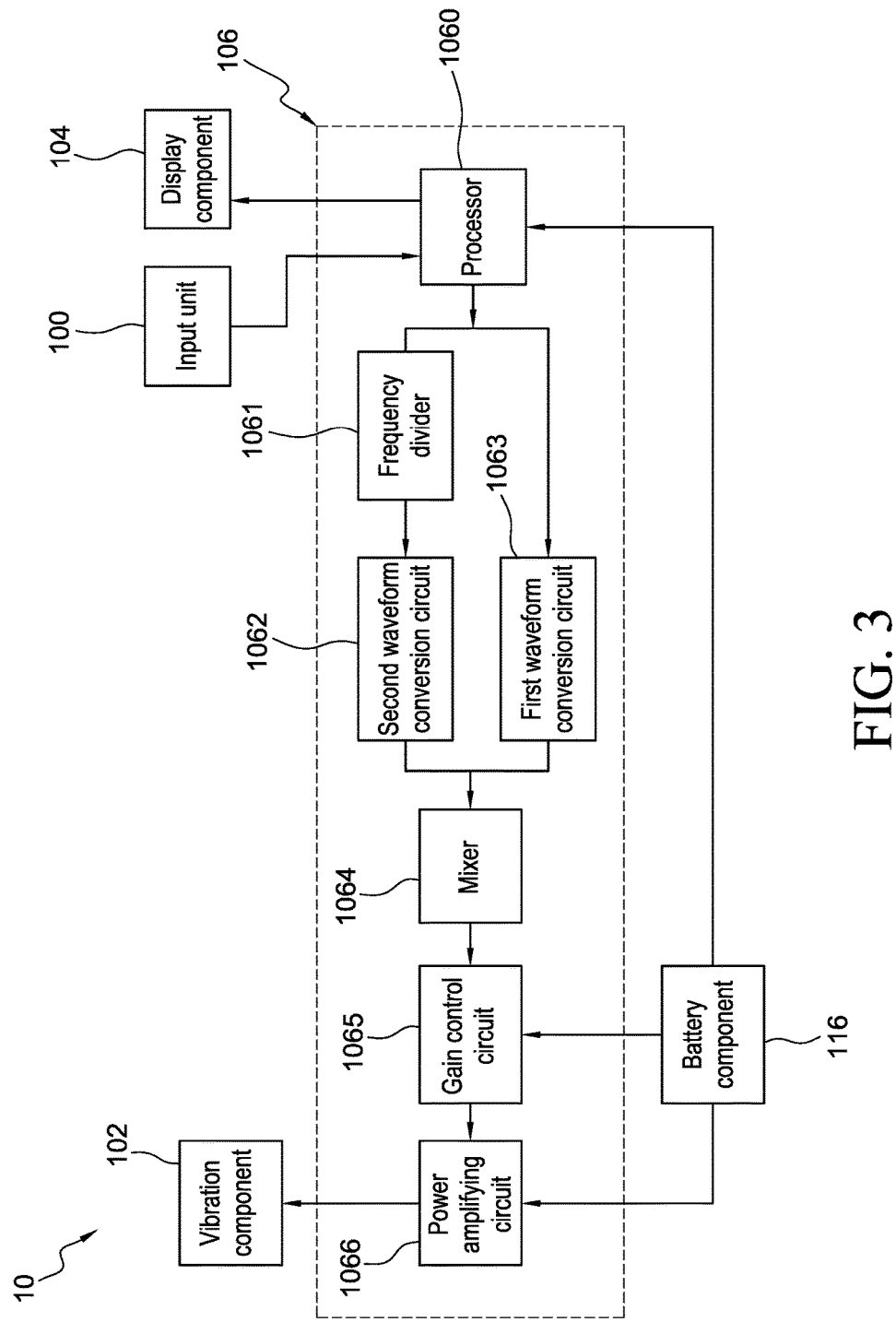
FIG. 3 illustrates a system block diagram of the electronic tuning fork device of FIGS. 1 and 2 of the current embodiment.

FIG. 3 illustrates a system block diagram of the electronic tuning fork device of FIGS. 1 and 2 of the current embodiment.

The control unit 106 is configured to control a vibration of the vibration component 102. As shown in FIG. 3, the control unit 106 includes a processor 1060, a frequency divider 1061, a second waveform conversion circuit 1062, a first waveform conversion circuit 1063, a mixer 1064, a gain control circuit 1065 and a power amplifying circuit 1066.

The processor 1060 is electrically connected to the input unit 100 and the display component 104, and is configured to generate a first square wave signal having a fixed frequency and to determine a gain parameter according to predetermined modes.

The frequency divider 1061 is electrically connected to the processor 1060 to receive the first square wave signal. The frequency divider 1061 then down-converts the first square wave signal and outputs a second square wave signal.

In the present embodiment, the first square wave signal is a 128 Hz square wave. The frequency divider 1061 receives the 128 Hz square wave, down-converts it to a 64 Hz square wave, and then outputs the 64 Hz square wave as the second square wave signal.

The processor 1060 generates the first square wave signal, (i.e., the 128 Hz signal via pulse width modulation ("PWM")). Other methods may be used to generate a square wave signal may be applied in the present invention.

64 Hz and 128 Hz frequencies are the two main frequency components that are detected from a vibrated metal tuning fork. The present invention may generate both of the two main frequencies for processing.

The first waveform conversion circuit 1063 is electrically connected to the processor 1060, and the first waveform conversion circuit 1063 is configured to convert the first square signal into a first sine wave signal. The second waveform conversion circuit 1062 is electrically connected to the frequency divider 1061, and the second waveform conversion circuit 1062 is configured to convert the second square signal into a second sine wave signal.

In an exemplary embodiment, the first waveform conversion circuit 1063 converts the 128 Hz square wave signal into a 128 Hz sine wave signal, and the second waveform conversion circuit 1062 converts the 64 Hz square wave signal into a 64 Hz sine wave signal.

The mixer 1064 is electrically connected to the first and the second waveform conversion circuits 1063 and 1062, to receive the 64 Hz and 128 Hz sine wave signals, for mixing. The mixer 1064 mixes the two signals respectively with the two frequencies, and then outputs a mixed signal to the gain control circuit 1065 for processing.

Figure 4:
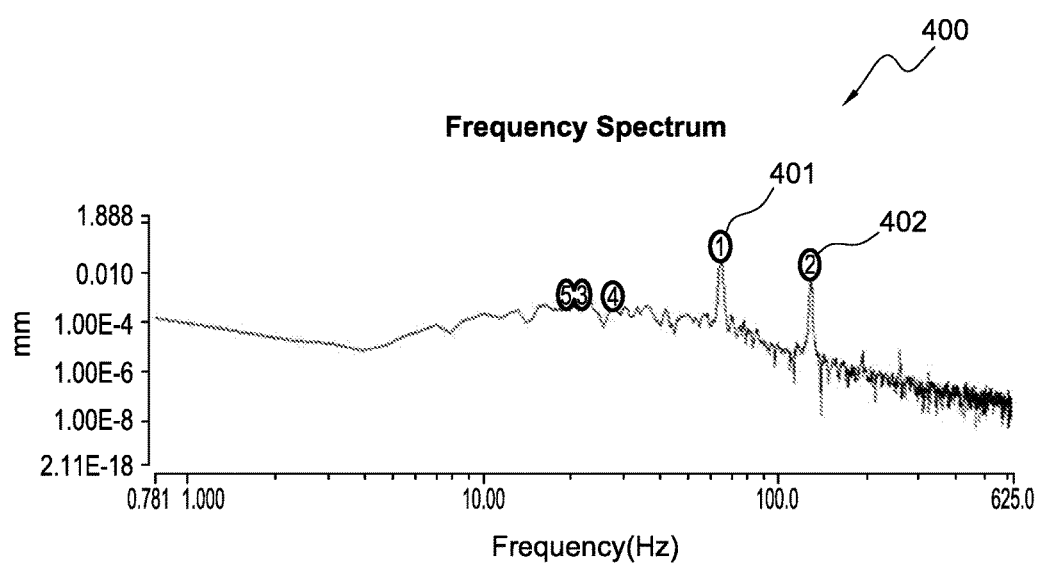
FIG. 4 illustrates a frequency spectrum diagram with a 64 Hz signal component and a 128 Hz signal component.

FIG. 4 illustrates a frequency spectrum 400 which illustrates the signal having a 64 Hz component 401 and a 128 Hz component 402.

The mixed signal includes two components, the 64 Hz signal and the 128 Hz signal. By outputting a signal with two components (64 Hz and 128 Hz), the mixer can simulate either a 64 Hz signal or a 128 Hz signal.

The gain control circuit 1065 is electrically connected to the processor 1060 and the mixer 1064 and is configured to change the amplitude of the sine wave signal transmitted from the mixer 1064 according to the gain parameter. If the gain parameter is the predetermined maximum value, the amplitude of the corresponding sine wave signal reaches the maximum; if the gain parameter is the predetermined minimum value, the amplitude of the corresponding sine wave signal reaches the minimum. The gain parameter, whether a predetermined maximum value or a predetermined minimum value, simulates a signal either increasing in amplitude (magnitude) from zero to a maximum or from a maximum to a zero.

In an alternative embodiment, the gain control circuit 1065 is electrically connected to the processor 1060 and the mixer 1064 and is configured to change the time value according to the gain parameter. If the gain parameter is the predetermined maximum value, the time reaches the maximum; if the gain parameter is the predetermined minimum value, the time reaches the minimum. The gain parameter, whether a predetermined maximum value or a predetermined minimum value, simulates a signal either increasing in time from zero to a maximum or from a maximum time to a zero.

The power amplifying circuit 1066 is electrically connected to the gain control circuit 1065 and the vibration component 102 and is configured to amplify an output signal of the gain control circuit 1065. The vibration component 102 is driven by an output signal of the power amplifying circuit 1066 to generate a vibration.

The battery component 116 is electrically connected to the processor 1060, the gain control circuit 1065 and the power amplifying circuit 1066. Referring back to FIG. 2, the control unit 106 may be implemented as a printed circuit board, such that the processor 1060, the first and second waveform conversion circuits 1063 and 1062, the gain control circuit 1065 and the power amplifying circuit 1066 may be implemented on the printed circuit board.

When measuring (i.e., testing), and the user cannot feel the vibration of the electronic tuning fork device 10, a control signal may be generated via the input unit 100, the processor 1060 receives the control signal and determines a corresponding gain parameter, and the processor 1060 may calculate a measurement result according to the corresponding gain parameter, the predetermined maximum value and the predetermined minimum value.

The measurement result is related to a ratio of the corresponding gain parameter and the predetermined maximum value or is related to a ratio of the corresponding gain parameter and the predetermined minimum value.

In an embodiment of the invention, the measurement result represents a vibration level of the vibration component 102, the processor 1060 may calculate a corresponding vibration level of the vibration component 102 through the ratio. The display unit 104 displays the measurement result, and the user may see the display unit 104 to obtain the measurement result.

The display unit 104 in the present embodiment is implemented by eight light emitting diodes (LEDs), which provide care takers more convenience to identify the reading, as comparing to a conventional tuning fork, in which care takers need to identify the reading by their naked eyes while the conventional tuning fork is still vibrating. However, the implementation of the display unit 104 is not limited to LEDs.

As shown in FIGS. 1-2, the eight LEDs are arranged in parallel, which makes the appearance of the LEDs' arrangement to be the same as a conventional metal tuning fork. When the electronic tuning fork is used by a care taker, the care taker can view the LEDs with the arrangement that is the same as the reading scales on the conventional metal tuning fork.

In one of the exemplary embodiments, a care taker presses the input unit 100 to begin the test for a diabetic. The vibration component 102 starts to vibrate at 128 Hz with a maximum amplitude. The total duration of a vibration of a 128 Hz signal in this exemplary embodiment is 30 seconds and the scale is divided into scales 1-8, in which scale 1 is with the maximum amplitude and scale 8 with the minimum amplitude. Each scale corresponds to one LED, and each timing interval will be approximately 3.33 seconds. Therefore, LED 1 will illuminate at 0 seconds-3.3 seconds, LED 2 will illuminate at 3.3 seconds-6.6 seconds, etc. to the scale 8. The care taker places the vibrating electronic tuning fork 10 at the diabetic's foot for example, and wait for the diabetic to tell the care taker when he or she cannot feel the vibration.

The vibration amplitude begins to decrease with time passes, and the lighting of the LEDs changes correspondingly. When the diabetic can no longer feel the vibration, the care taker again presses the input unit 100. The reading of the lighting stops at which LED will be the measurement result, for the care taker to determine whether the diabetic's perception is normal.

In an alternative embodiment, a display screen may include a LCD screen with a graphical representation of the measurement, including for example, images or numbers to represent the 0-8 scale.

The electronic tuning fork of the present invention may further include a speaker (not illustrated). The speaker may be connected to the processor, for speaking measurement result (i.e., the reading) after the measurement. The speaker provides diabetics who perform the measurement by themselves with the convenience over listening to the result rather than reading the result by their eyes.

In an alternative embodiment of the present invention, the control unit 106 may further include a wireless communication circuit (not illustrated).

The wireless communication circuit is electrically connected to the processor 1060, and is configured to wirelessly transmit the measurement result to an external device. The external device may be a smart phone, a personal computer, a tablet and a laptop. Preferably, the wireless communication circuit may be, but not limited to, implemented by a Bluetooth Low Energy (BLE) 4.0 chip. The communication standard of the wireless communication circuit communicates with the external device is not limited, the communication standard may be 2G standard, 3G standard, 4G standard or WiFi.

The electronic tuning fork device 10 as provided according to the embodiments of the present invention is convenient for patients to carry and allows the patient to perform the measurement (testing) at home by himself/herself or by other people Therefore, the present invention significantly eliminates the inconvenience of using a mechanical tuning fork and improves the accuracy of the measurement, and thus achieves a significant improvement in the relevant field.

The electronic tuning fork device 10 may also be applied to a patient's finger, or other parts to detect the sense of peripheral nerves, which expands the usage of the electronic tuning fork device 10 of the present invention. The convenience provided by the electronic tuning fork device 10 of the present invention makes that the device 10 can be manipulated not only by experienced or trained care takers such as doctors or nurses, but also to all any other people without relevant medical experience or training.

In sum, the electronic tuning fork device 10 of the present invention breaks the limitation that a conventional metal tuning fork can be only performed by experienced or trained medical staffs. The device 10 of the present invention provides a performer with convenience to read the scale by the LEDs on the electronic tuning fork device 10. The electronic tuning fork device 10 starts vibrating when the input unit (i.e., the button) is pressed, which renders the traditional way of vibration by knocking the metal tuning fork obsolete.

As described above, optimal embodiments of the present invention have been disclosed in the drawings and the present specification. In this case, although specific terms have been used, those terms are merely intended to describe the present invention and are not intended to limit the meanings and the scope of the present invention as disclosed in the accompanying claims. Therefore, those skilled in the art will appreciate that various modifications and other equivalent embodiments are also possible given the above description. Therefore, the technical scope of the present invention should be defined by the technical spirit of the accompanying claims.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An electronic tuning fork device, comprising:
a control unit including a processor, electrically connected to an input unit and a display component, wherein the processor is configured to generate a first square wave signal and determine a gain parameter according to a predetermined mode, wherein the gain parameter is a value selected from between a predetermined maximum value and a predetermined minimum value;
a frequency divider electrically connected to the processor, configured to down-convert the first square wave signal and output a second square wave signal;
a first waveform conversion circuit, electrically connected to the processor, configured to convert the first square wave signal into a first sine wave signal;
a second waveform conversion circuit, electrically connected to the frequency divider, configured to convert the second square wave signal into a second sine wave signal;
a mixer, electrically connected to the first and second waveform conversion circuits, configured to mix the first sine wave signal and the second sine wave signal and output a sine wave signal, and
a gain control circuit, electrically connected to the processor and the mixer, configured to change an amplitude of the sine wave signal according to the gain parameter, wherein
when a control signal is generated, the processor receives the control signal and determines a corresponding gain parameter, the processor calculates a measurement result according to the corresponding gain parameter, the predetermined maximum value and the predetermined minimum value.

2. The electronic tuning fork device according to claim 1, further comprising: the display component, configured to display the measurement result,
the control unit configured to control a vibration of a vibration component,
a power amplifying circuit, electrically connected to the gain control circuit and the vibration component, configured to amplify an output signal of the gain control circuit, and
a battery component, electrically connected to the processor, the gain control circuit and the power amplifying circuit.

3. The electronic tuning fork device according to claim 1, wherein in the predetermined mode, the gain parameter gradually decreases from the predetermined maximum value to the predetermined minimum value within a predetermined time.

4. The electronic tuning fork device according to claim 1, wherein in the predetermined mode, the gain parameter gradually increases from the predetermined minimum value to the predetermined maximum value within a predetermined time.

5. The electronic tuning fork device according to claim 1, wherein the input unit includes:
   a remote transmitter, configured to transmit a wireless signal; and
   a remote receiver, electronically connected to the processor, and configured to receive the wireless signal.

6. The electronic tuning fork device according to claim 2, wherein the vibration component is a vibration speaker.

7. The electronic tuning fork device according to claim 1, wherein the control unit further includes a wireless communication circuit, wherein the wireless communication circuit is electronically connected to the processor, and is configured to wirelessly transmit the measurement result to an external device.

8. The electronic tuning fork device according to claim 1, further comprising a speaker, wherein the speaker is electronically connected to the processor, and is configured to play the measurement result in a voice manner.

9. The electronic tuning fork device according to claim 1, wherein the square wave signal has a fixed frequency.

10. The electronic tuning fork device according to claim 1, wherein the measurement result is related to a ratio of the corresponding gain parameter and the predetermined maximum value or related to a ratio of the corresponding gain parameter and the predetermined minimum value.

* * * * *